(12) United States Patent
Hong et al.

(10) Patent No.: US 11,014,861 B1
(45) Date of Patent: May 25, 2021

(54) METHOD FOR CO-PRODUCING 2,3,3,3-TETRAFLUOROPROPENE AND TRANS-1,3,3,3-TETRAFLUOROPROPENE

(71) Applicant: Zhejiang Quhua Fluor-Chemistry Co Ltd, Zhejiang (CN)

(72) Inventors: Jiangyong Hong, Zhejiang (CN); Bo Yang, Zhejiang (CN); Hao Ouyang, Zhejiang (CN); Yan Zhang, Zhejiang (CN); Yang Zhao, Zhejiang (CN)

(73) Assignee: Zhejiang Quhua Fluor-Chemistry Co Ltd, Zhejiang (CN)

( * ) Notice: Subject to any disclaimer, the term of this patent is extended or adjusted under 35 U.S.C. 154(b) by 314 days.

(21) Appl. No.: 16/337,409

(22) PCT Filed: Jun. 25, 2018

(86) PCT No.: PCT/CN2018/000233
§ 371 (c)(1),
(2) Date: Mar. 28, 2019

(87) PCT Pub. No.: WO2019/075932
PCT Pub. Date: Apr. 25, 2019

(30) Foreign Application Priority Data

Oct. 19, 2017 (CN) .......................... 201710976257.4

(51) Int. Cl.
*C07C 17/20* (2006.01)
*B01J 23/26* (2006.01)
(Continued)

(52) U.S. Cl.
CPC ............. *C07C 17/206* (2013.01); *B01J 23/08* (2013.01); *B01J 23/10* (2013.01); *B01J 23/26* (2013.01); *C07C 21/18* (2013.01)

(58) Field of Classification Search
CPC ........ C07C 17/206; C07C 21/18; B01J 23/26; B01J 23/08; B01J 23/10
See application file for complete search history.

(56) References Cited

U.S. PATENT DOCUMENTS

2009/0240090 A1  9/2009  Merkel et al.
2017/0320797 A1* 11/2017  Lv ............................ B01J 23/72

FOREIGN PATENT DOCUMENTS

CN          1852880      10/2006
CN        101028992       9/2007
(Continued)

OTHER PUBLICATIONS

"International Search Report (Form PCT/ISA/210)", dated Sep. 20, 2018, pp. 1-5.

*Primary Examiner* — Jafar F Parsa
(74) *Attorney, Agent, or Firm* — JCIPRNET

(57) ABSTRACT

Disclosed is a method for co-producing 2,3,3,3-tetrafluoropropene and trans-1,3,3,3-tetrafluoropropene, comprising the following steps: preheating a mixture of 1,1,1,2,2-pentachloropropane and 1,1,1,3,3-pentachloropropane together with anhydrous hydrogen fluoride and simultaneously introducing into a first reactor to react in the presence of a catalyst $La_2O_3$—$Cr_2O_3$ to obtain a first reactor product; directly introducing the first reactor product into a second reactor without separation, and carrying out a catalytic fluorination reaction in the presence of a catalyst $Ga_2O_3$—$Y_2O_3$—$Cr_2O_3$ to obtain a second reactor product; and separating the second reactor product to obtain the products of 2,3,3,3-tetrafluoropropene and trans-1,3,3,3-tetrafluoropropene. The invention has such advantages that the process is simple and less equipment investment is required; used catalysts have good activity, high selectivity and long total (Continued)

life; and the ratio of the two products can be flexibly adjusted according to market demands.

7 Claims, 1 Drawing Sheet

(51) Int. Cl.
*B01J 23/10* (2006.01)
*B01J 23/08* (2006.01)
*C07C 21/18* (2006.01)

(56) References Cited

FOREIGN PATENT DOCUMENTS

| | | |
|---|---|---|
| CN | 101215220 | 7/2008 |
| CN | 102001910 | 4/2011 |
| CN | 104710274 | 6/2015 |
| CN | 107721809 | 2/2018 |
| WO | 2009015317 | 1/2009 |
| WO | 2010/123148 | 10/2010 |
| WO | 2016132111 | 8/2016 |

* cited by examiner

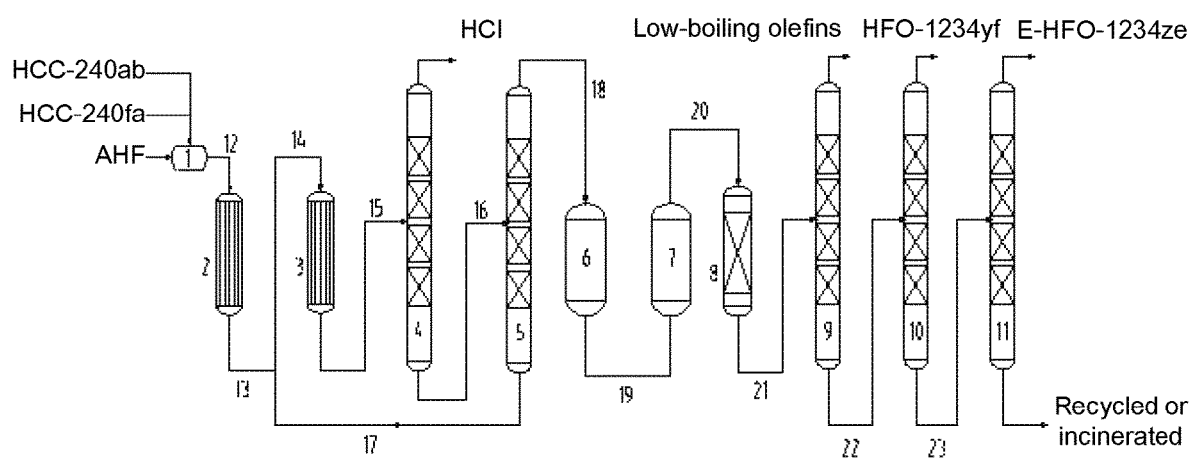

US 11,014,861 B1

METHOD FOR CO-PRODUCING 2,3,3,3-TETRAFLUOROPROPENE AND TRANS-1,3,3,3-TETRAFLUOROPROPENE

CROSS-REFERENCE TO RELATED APPLICATION

This application is a 371 of international application of PCT application serial No. PCT/CN2018/000233, filed on Jun. 25, 2018, which claims the priority benefit of China application No. 201710976257.4, filed on Oct. 19, 2017. The entirety of each of the above-mentioned patent applications is hereby incorporated by reference herein and made a part of this specification.

BACKGROUND OF THE INVENTION

1. Technical Field

The invention relates to the technical field of fluoroolefins, in particular to a method for co-producing 2,3,3,3-tetrafluoropropene and trans-1,3,3,3-tetrafluoropropene.

2. Background Art

As a trending research topic in the world, fluorine refrigerant substitutes require an ozone depletion potential (ODP) of 0, a global warming potential (GWP) as low as possible, and life circle climate performance as short as possible, while its thermodynamic properties are as close as possible to those of the currently used HFC-134a, HCFC-22, R410A, R407C, etc., to reduce the cost of refrigeration device transformation caused by the substitutes.

2,3,3,3-tetrafluoropropene (HFO-1234yf) has a boiling point of −29.5° C., has excellent environmental parameters: GWP≤1, life cycle climate performance (LCCP) of 10.5 days only, far lower than LCCP of HFC-134a, and the same atmospheric decomposition products as HFC-134a. Furthermore, its system performance is better than that of HFC-134a. If HFO-1234yf is used to substitute the HFC-134a refrigerant, automobile manufacturers can continue to use the original MAC (Mobile Air-Conditioning) system. Therefore, HFO-1234yf is considered to be a potential new generation of automobile refrigerant substitutes. It has been accepted by automobile manufacturers in Western Europe and has been gradually promoted in commercial applications since 2011.

Trans-1,3,3,3-tetrafluoropropene (E-HFO-1234ze) has a boiling point of −19° C., excellent environmental performance: GWP≤1, LCCP of 16.4 days only, far lower than LCCP of HFC-134a, and the same atmospheric decomposition products as HFC-134a. E-HFO-1234ze can be used as a refrigerant and can substitute HFC-245fa as a foaming agent, a cleaning agent, a solvent, and the like.

US2009/0240090 describes the reaction of 1,1,1,2,3-pentachloropropane (HCC-240db) in the absence of oxygen to obtain 2-chloro-3,3,3-trifluoropropene (HCFO-1233xf). The obtained HCFO-1233xf is converted into 2-chloro-1,1,1,2-tetrafluoropropane (HCFC-244bb) by a liquid phase method, and then gas phase fluorinated to HFO-1234yf. The steps of the process are longer and the reaction temperature in the final step is as high as 460° C.

WO2009/015317 describes reaction of hydrogen fluoride (HF) with chlorinated compounds such as 1,1,2,3-tetrachloropropene (HCO-1230xa), HCC-240db or 2,3,3,3-tetrachloropropene (HCO-1230x0 in a gas phase. The method can be used to obtain HCFO-1233xf, but the catalyst used can only work continuously for 67 hours, and the life of the catalyst is still short after the addition of a stabilizer.

WO2010/123148 describes the fluorination of HCC-240db to HCFO-1233xf in the absence of a catalyst. However, the reaction temperature is high, and the HCFO-1233xf selectivity is only 73%.

US2009/0240090 discloses a method of synthesizing HFO-1234yf. According to the method, a raw material, 1,1,2,3-tetrachloropropene is first subjected to HF gas phase fluorination in a first reactor in the presence of a catalyst $Cr_2O_3$ to obtain 2-chloro-3,3,3-trifluoropropene (HCFC-1233xf); then, HCFO-1233xf is subjected to HF liquid phase fluorination in a second reactor in the presence of $SbCl_5$ to obtain 2-chloro-1,1,1,2-tetrafluoropropane (HCFC-244bb); finally, HCFC-244bb is subjected to dehydrochlorination in a third reactor in the presence of $CsCl/MgF_2$ at a temperature of 350-550° C. to obtain HFO-1234yf. However, the method requires three steps of reaction; and the second step is a liquid phase catalytic reaction in which the intermediate product HCFC-244bb needs to be separated as a raw material for the third reaction step, and the catalyst has a short life.

CN1852880 discloses fluorination of HCFO-1233zd to 1-chloro-1,3,3,3-tetrafluoropropane and 1,1,1,3,3-pentafluoropropane in the presence of a fluorination catalyst, followed by HF removal in the presence of a liquid-phase strong base to obtain HFO-1234ze. This method produces a large amount of waste lye, which brings environmental problems.

CN200710090535 and CN200810000765 disclose a method for preparing HFO-1234ze from 1,1,1,3,3-pentachloropropane in the presence of a fluorination catalyst, where 1,1,1,3,3-pentachloropropane is first fluorinated to HCFO-1233zd and a small amount of HFC-245fa, and then further fluorinated to obtain HFO-1234ze, and the product is subjected to rectification to obtain HFO-1234ze.

However, the above-mentioned invention has problems such as a long preparation route, a large amount of by-products, and a short catalyst life.

SUMMARY OF THE INVENTION

The invention is directed to the deficiencies of the prior art, and provides a method for co-producing 2,3,3,3-tetrafluoropropene and trans-1,3,3,3-tetrafluoropropene, which has the advantages of simple process, high reaction efficiency, long catalyst life and high operation flexibility.

In order to solve the above technical problems, the technical solution adopted by the invention is: a method for co-producing 2,3,3,3-tetrafluoropropene and trans-1,3,3,3-tetrafluoropropene, comprising the following steps:

(1) Preheating a mixture of 1,1,1,2,2-pentachloropropane and 1,1,1,3,3-pentachloropropane together with anhydrous hydrogen fluoride and simultaneously introducing into a first reactor to react in the presence of a catalyst $La_2O_3$—$Cr_2O_3$ at a reaction temperature of 200-350° C., a molar ratio of the anhydrous hydrogen fluoride to the mixture of 1,1,1,2,2-pentachloropropane and 1,1,1,3,3-pentachloropropane is 6-18:1, with a contact time of 1-20s to obtain a first reactor product;

(2) directly introducing the first reactor product obtained in the step (1) into a second reactor without separation, and carrying out a catalytic fluorination reaction in the presence of a catalyst $Ga_2O_3$—$Y_2O_3$—$Cr_2O_3$ at a reaction temperature of 250-400° C. with a contact time of 1-35s to obtain a second reactor product;

(3) introducing the second reactor product obtained in the step (2) into a first separation column for separation to obtain a first separation column bottom component and hydrogen chloride;

(4) introducing the first separation column component obtained in the step (3) into a second separation column for separation to obtain a second separation column overhead component and a second separation column bottom component;

(5) washing the second separation column overhead component obtained in the step (4) with water and an alkali, drying, and then introducing into a third separation column to obtain a third separation column overhead component and a third separation column bottom component;

(6) introducing the third separation column bottom component obtained in the step (5) into a fourth separation column to obtain a 2,3,3,3-tetrafluoropropene product and a fourth separation column bottom component; and (7) introducing the fourth separation column bottom component obtained in the step (6) into a fifth separation column to obtain a trans-1,3,3,3-tetrafluoropropene product.

As a preferred embodiment of the invention, the molar ratio of 1,1,1,2,2-pentachloropropane to 1,1,1,3,3-pentachloropropane in the mixture of 1,1,1,2,2-pentachloropropane and 1,1,1,3,3-pentachloropropane in the step (1) is preferably 1:0.05-20.

As a preferred embodiment of the invention, the molar ratio of the anhydrous hydrogen fluoride to the mixture of 1,1,1,2,2-pentachloropropane and 1,1,1,3,3-pentachloropropane in the step (1) is preferably 8-15:1, the reaction temperature is preferably 250-300° C., and the contact time is preferably 2-10s.

As a preferred embodiment of the invention, the reaction temperature in the step (2) is preferably 280-330° C., and the contact time is preferably 4-15s.

As a preferred embodiment of the invention, the catalyst $La_2O_3$—$Cr_2O_3$ in the step (1) preferably comprises 0.5-20 wt % (wt %, percentage by weight) of $La_2O_3$ and 80-99.5 wt % of $Cr_2O_3$.

As a preferred embodiment of the invention, the catalyst $Ga_2O_3$—$Y_2O_3$—$Cr_2O_3$ in the step (2) preferably comprises 1-15 wt % of $Ga_2O_3$, 3-20 wt % of $Y_2O_3$, and 65-96 wt % of $Cr_2O_3$.

As a preferred embodiment of the invention, the second separation column bottom component in the step (4) can be circulated to the first reactor.

The main compounds involved in the invention have the following boiling points:

| Chemical name | Chemical naming | Chemical formula | Boiling point/° C. |
|---|---|---|---|
| 1,1,1,2,2-pentachloropropane | HCC-240ab | $CCl_3CCl_2CH_3$ | 173 |
| 1,1,1,3,3-pentachloropropane | HCC-240fa | $CCl_3CH_2CHCl_2$ | 180 |
| 2,3,3,3-tetrafluoropropene | HFO-1234yf | $CF_3CF=CH_2$ | −29.5 |
| 1,3,3,3-tetrafluoropropene | HFO-1234ze | $CF_3CH=CHF$ | −19 (trans), 9.8 (cis) |
| 2-chloro-3,3,3-trifluoropropene | HCFO-1233xf | $CF_3CCl=CH_2$ | 15 |
| 1-chloro-3,3,3-trifluoropropene | HCFO-1233zd | $CF_3CH=CHCl$ | 18.3 (trans), 38 (cis) |
| Anhydrous hydrogen fluoride | AHF | HF | 19 |
| Hydrogen chloride | HCl | HCl | −85 |

According to the invention, 1,1,1,2,2-pentachloropropane, 1,1,1,3,3-pentachloropropane and anhydrous hydrogen fluoride (AHF) are used as raw materials, and are synthesized into 2,3,3,3-tetrafluoropropene and trans-1,3,3,3-tetrafluoropropene by two-step gas phase catalytic fluorination; in the first step of reaction, the raw materials 1,1,1,2,2-pentachloropropane, 1,1,1,3,3-pentachloropropane and anhydrous hydrogen fluoride are gasified and then enter a first reactor to react in the presence of a catalyst; 1,1,1,2,2-pentachloropropane reacts with AHF to obtain 2-chloro-3,3,3-trifluoropropene and hydrogen chloride; 1,1,1,3,3-pentachloropropane reacts with AHF to obtain 1-chloro-3,3,3-trifluoropropene and hydrogen chloride; the conversion rate of pentachloropropane (HCC-240) can reach 100%. The reaction conditions are: the molar ratio of HF to HCC-240 of 6-18:1, a reaction temperature of 200-350° C., and a contact time is 1-20s. The preferred reaction conditions are that: the molar ratio of HF to HCC-240 being 8-15:1, a reaction temperature of 250-300° C., and a contact time of 2-10s. In the invention, HCC-240 may be composed of HCC-240ab and HCC-240fa in any molar ratio, and the molar ratio of HCC-240ab to HCC-240fa is preferably 1:0.05-20.

According to the invention, in the second step of reaction, the reaction product at an outlet of the first reactor directly enters a second reactor and reacts in the presence of a catalyst. The AHF of the first step of reaction is greatly excessive and can promote the complete conversion of HCC-240; the excessive AHF and the product flow enter the second reactor, which facilitates deep fluorination, and the second reactor performs two main reactions: (1) conversion of HCFO-1233zd to E-HFO-1234ze; (2) conversion of HCFO-1233xf to HFO-1234yf. The reaction conditions are: a reaction temperature of 250-400° C., a contact time of 1-35s, and the preferred reaction conditions are: a reaction temperature of 280-330° C., and a contact time of 4-15s.

In the invention, the form of the first reactor and the second reactor and the material used are not limited, and any suitable gas phase fluorination reactor is suitable for the invention, and a tubular reactor made of a material resistant to hydrogen fluoride corrosion such as Hastelloy or Inconel is preferred.

In the invention, the product formed by the second step of reaction enters a first separation column for separation; a first separation column overhead component (HCl) is collected to a designated storage tank; a first separation column bottom component which mainly includes HFO-1234yf, E-HFO-1234ze and AHF enters a second separation column for separation. A second separation column bottom component which includes AHF and a small amount of HCFO-1233xf and HCFO-1233zd is directly recycled to the second reactor, and can also be separated by cooling to remove organic substances HCFO-1233xf and HCFO-1233zd and then recycled to the second reactor; a second separation column overhead component which mainly includes HFO-1234yf and E-HFO-1234ze enters a product aftertreatment system to be washed with water and an alkali and dried to enter a third separation column. A very small amount of light component olefin impurities are rectified at the overhead of the third separation column, and the mixture mainly comprising HFO-1234yf and E-HFO-1234ze obtained at the bottom of the third separation column enters a fourth separation column. HFO-1234yf produced at the overhead of the fourth separation column and a mixture of E-HFO-1234ze and a small amount of high-boiling residues, obtained at the bottom of the fourth separation column, enter a fifth separation column. When accumulated to a certain amount, E-HFO-1234ze produced at the overhead of the fifth separation column and high-boiling residues obtained at the bottom of the fifth separation column are recycled or sent to be incinerated. In the invention, the form and operating conditions of the separation columns are not limited, and may be appropriately selected depending on the components to be separated, the operating conditions of the reaction system, and the like.

In the invention, the fluorination catalyst used in the first step of reaction may be chromium oxide, chromium fluoride, fluorinated chromium oxide, lanthanum oxide, lanthanum fluoride, fluorinated lanthanum oxide and mixtures thereof, preferably a mixture composed of 0.5-20 wt % of $La_2O_3$ and 80-99.5 wt % of $Cr_2O_3$ and mixtures composed of fluorinated oxides thereof, more preferably a mixture composed of 1-15 wt % of $La_2O_3$ and 85-99.5 wt % of $Cr_2O_3$ and mixtures composed of fluorinated oxides thereof. The fluorination catalyst used in the second step of reaction may be chromium oxide, chromium fluoride, fluorinated chromium oxide, gallium oxide, gallium fluoride, fluorinated gallium oxide, yttrium oxide, yttrium fluoride, fluorinated yttrium oxide and mixtures thereof, preferably a mixture composed of 1-15 wt % of $Ga_2O_3$, 3-20 wt % of $Y_2O_3$, and 65-96 wt % of $Cr_2O_3$ and mixtures of fluorinated oxides thereof, more preferably a mixture composed of 2-13 wt % of $Ga_2O_3$, 5-16 wt % of $Y_2O_3$, and 74-82 wt % of $Cr_2O_3$ and mixtures of fluorinated oxides thereof.

In the invention, the catalyst used in the first reactor may be prepared by blending or coprecipitation well known in the art. For example, chromium chloride and barium chloride can be dissolved in water in a certain ratio and react with a precipitating agent; the pH of the solution is adjusted to weakly alkaline, the solution is then stirred, precipitated, filtered, and dried at 100-150° C. and calcined at 360° C. to form a catalyst precursor; after compression molding, the catalyst precursor is load in the first reactor and activated by introducing anhydrous hydrogen fluoride diluted with nitrogen.

In the invention, the catalyst used in the second reactor may be prepared by blending or coprecipitation well known in the art. For example, chromium chloride, gallium chloride and yttrium chloride can be dissolved in water in a certain ratio and react with a precipitating agent; the pH of the solution is adjusted to weakly alkaline, the solution is then stirred, precipitated, filtered, and dried at 100-150° C. and calcined at 400° C. to form a catalyst precursor; after compression molding, the catalyst precursor is load in the second reactor and activated by introducing anhydrous hydrogen fluoride diluted with nitrogen.

In the invention, the fluorination catalysts used in the first step of reaction and the second step of reaction have good activity, high selectivity, good regeneration performance and long total life. After the catalytic performance of the fluorination catalysts is reduced, the catalytic performance can be regenerated and thus the fluorination catalysts can be recycled. When the catalysts used in the first reactor and the second reactor are regenerated, air is first slowly introduced in a 350° C. nitrogen atmosphere to burn carbon deposit on the surfaces of the catalysts for 12h; then hydrogen is introduced to reduce the catalysts for 3h; finally, AHF is introduced in a nitrogen atmosphere for activation for 5h.

Compared with the prior art, the invention has the following advantages:

1. the process is simple, and a set of reaction device can simultaneously produce two products, which greatly simplifies the process flow;

2. the reaction efficiency is high, the conversion rate and the target product selectivity are high, the conversion rate of HCC-240 is 100%, and the total selectivity of E-HFO-1234ze and HFO-1234yf is 98% or above;

3. the catalysts have a long total life; through multi-metal synergistic action, assisted catalysis and inhibition of crystal form, catalysts of the invention are improved in stability and selectivity and increased in service life with the single-pass life of more than 200 days, and can operate stably for more than 110 days after being regenerated once;

4. the investment is small, the operation flexibility is good, and the production ratio of 2,3,3,3-tetrafluoropropene and trans-1,3,3,3-tetrafluoropropene can be flexibly adjusted according to market demands; and 5, with safety and environmental friendliness, the invention uses a two-step gas phase reaction, unreacted raw materials and intermediates can be recycled, the catalysts can be recycled after regeneration, further reducing the three-waste emissions.

BRIEF DESCRIPTION OF THE DRAWINGS

FIG. 1 is a process flow diagram of the invention.

As shown in the figure: 1 refers to vaporizer, 2 refers to first reactor, 3 refers to second reactor, 4 refers to first separation column, 5 refers to second separation column, 6 refers to water washing column, 7 refers to alkali washing column, 8 refers to dryer, 9 refers to third separation column, 10 refers to fourth separation column, 11 refers to fifth separation column, and 12, 13, 14, 15, 16, 17, 18, 19, 20, 21, 22, 23 refer to pipelines.

DETAILED DESCRIPTION OF THE EMBODIMENTS

The process of the invention is as shown in FIG. 1. A first reactor 2 and a second reactor 3 are respectively loaded with different catalysts, and HCC-240ab and HCC-240fa are mixed in a certain ratio, and then mixed with AHF through a vaporizer 1 to be heated and vaporized; the mixture enters the first reactor 2 through a pipeline 12 to have a reaction; the mixture containing HCFO-1233xf, HCFO-1233zd, hydrogen chloride and excessive AHF directly enters the second reactor 3 through pipelines 13, 14 to have a reaction; and the material out of the outlet of the second reactor 3 enters a first separation column 4 through a pipeline 15, and HCl is dry separated from the overhead of the first separation column 4 and stored separately. The material at the bottom of the first separation column 4 enters a second separation column 5 through pipeline 16. A mixture of AHF and a small amount of unreacted HCFO-1233zd and HCFO-1233xf, obtained at the bottom of the second separation column 5 is circulated to the second reactor 3 through pipelines 17, 14 to have a re-reaction; the overhead component of the second separation column 5 is a mixture mainly containing HFO-1234yf and E-HFO-1234ze, and the mixture enters a water washing column 6 for acid removal through a pipeline 18, then enters an alkali washing column 7 for further acid removal through a pipeline 19, then enters a dryer 8 for moisture removal through a pipeline 20, and then enters a third separation column 9 for light component removal through a pipeline 21; and a tiny amount of low-boiling fluorine-containing olefin impurities obtained at the overhead of the third separation column 9 and a material flow of HFO-1234yf and E-HFO-1234ze obtained at the bottom of the third separation column 9 enter a fourth separation column 10 through a pipeline 22. HFO-1234yf produced at the overhead of the fourth separation column 10 and an E-HFO-1234ze-enriched material flow obtained at the bottom of the fourth separation column 10 enter a fifth separation column 11 through the pipeline 23. When accumulated to a certain amount, E-HFO-1234ze produced at the overhead of the fifth separation column 11 and heavy components obtained at the bottom are recycled or sent to be incinerated.

The invention is further described in detail below by means of embodiments, but the invention is not limited to the embodiments described.

Embodiment 1

300 ml of a catalyst $La_2O_3$—$Cr_2O_3$ (composing 1 wt % of $La_2O_3$ and 99 wt % of $Cr_2O_3$) is loaded into a first reactor, heated to 250° C., and activated by introducing anhydrous hydrogen fluoride diluted with nitrogen. The flow rate of AHF is 25 g/h, the flow rate of nitrogen is 0.2 L/min, and the activation time is 8 hours.

300 ml of a catalyst $Ga_2O_3$—$Y_2O_3$—$Cr_2O_3$ (composing 1 wt % of $Ga_2O_3$, 3 wt % of $Y_2O_3$ and 96 wt % of $Cr_2O_3$) is loaded into a second reactor, heated to 280° C., and activated by introducing anhydrous hydrogen fluoride diluted with nitrogen. The flow rate of AHF is 25 g/h, the flow rate of nitrogen is 0.2 L/min, and the activation time is 8 hours.

After the activation is completed, HCC-240ab, HCC-240fa and hydrogen fluoride are mixed and then introduced in a vaporizer; the vaporized mixture enters the first reactor for reaction after the temperature of the vaporized mixture is slightly lower than the temperature of the first reactor, wherein the temperature of the first reactor is controlled to be 250° C., the molar ratio of anhydrous hydrogen fluoride to 1,1,1,2,2-pentachloropropane to 1,1,1,3,3-pentachloropropane is 16:1:1, and the contact time is 10s. The material at an outlet of the first reactor is directly sent to the second reactor for reaction, wherein the reaction temperature of the second reactor is 280° C., and the contact time is 10s. A bypass is connected to the outlet of the first reactor for sampling analysis. The product is washed with water and an alkali before analysis. The composition of the organic product is then analyzed by gas chromatography. The results are shown in Table 1. The product at the outlet of the second reactor was washed with water and alkali, and the composition of the organic product was analyzed by gas chromatography. The results are shown in Table 2.

Embodiment 2

300 ml of a catalyst $La_2O_3$—$Cr_2O_3$ (composing 3 wt % of $La_2O_3$ and 97 wt % of $Cr_2O_3$) is loaded into a first reactor, heated to 250° C., and activated by introducing anhydrous hydrogen fluoride diluted with nitrogen. The flow rate of AHF is 25 g/h, the flow rate of nitrogen is 0.2 L/min, and the activation time is 8 hours.

300 ml of a catalyst $Ga_2O_3$—$Y_2O_3$—$Cr_2O_3$ (composing 3 wt % of $Ga_2O_3$, 5 wt % of $Y_2O_3$ and 92 wt % of $Cr_2O_3$) is loaded into a second reactor, heated to 280° C., and activated by introducing anhydrous hydrogen fluoride diluted with nitrogen. The flow rate of AHF is 25 g/h, the flow rate of nitrogen is 0.2 L/min, and the activation time is 8 hours.

After the activation is completed, HCC-240ab, HCC-240fa and hydrogen fluoride are mixed and then introduced in a vaporizer; the vaporized mixture enters the first reactor for reaction after the temperature of the vaporized mixture is slightly lower than the temperature of the first reactor, wherein the temperature of the first reactor is controlled to be 250° C., the molar ratio of anhydrous hydrogen fluoride to 1,1,1,2,2-pentachloropropane to 1,1,1,3,3-pentachloropropane is 20:1:1, and the contact time is 7.2s. The material at an outlet of the first reactor is directly sent to the second reactor for reaction, wherein the reaction temperature of the second reactor is 280° C., and the contact time is 7.2s. A bypass is connected to the outlet of the first reactor for sampling analysis. The product is washed with water and an alkali before analysis. The composition of the organic product is then analyzed by gas chromatography. The results are shown in Table 1. The product at the outlet of the second reactor was washed with water and alkali, and the composition of the organic product was analyzed by gas chromatography. The results are shown in Table 2.

Embodiment 3

300 ml of a catalyst $La_2O_3$—$Cr_2O_3$ (composing 8 wt % of $La_2O_3$ and 92 wt % of $Cr_2O_3$) is loaded into a first reactor, heated to 270° C., and activated by introducing anhydrous hydrogen fluoride diluted with nitrogen. The flow rate of AHF is 25 g/h, the flow rate of nitrogen is 0.2 L/min, and the activation time is 8 hours.

300 ml of a catalyst $Ga_2O_3$—$Y_2O_3$—$Cr_2O_3$ (composing 5 wt % of $Ga_2O_5$, 7 wt % of $Y_2O_3$ and 88 wt % of $Cr_2O_3$) is loaded into a second reactor, heated to 290° C., and activated by introducing anhydrous hydrogen fluoride diluted with nitrogen. The flow rate of AHF is 25 g/h, the flow rate of nitrogen is 0.2 L/min, and the activation time is 8 hours.

After the activation is completed, HCC-240ab, HCC-240fa and hydrogen fluoride are mixed and then introduced in a vaporizer; the vaporized mixture enters the first reactor for reaction after the temperature of the vaporized mixture is slightly lower than the temperature of the first reactor, wherein the temperature of the first reactor is controlled to be 270° C., the molar ratio of anhydrous hydrogen fluoride to 1,1,1,2,2-pentachloropropane to 1,1,1,3,3-pentachloropropane is 20:1:1, and the contact time is 6s. The material at an outlet of the first reactor is directly sent to the second reactor for reaction, wherein the reaction temperature of the second reactor is 290° C., and the contact time is 6s. A bypass is connected to the outlet of the first reactor for sampling analysis. The product is washed with water and an alkali before analysis. The composition of the organic product is then analyzed by gas chromatography. The results are shown in Table 1. The product at the outlet of the second reactor was washed with water and alkali, and the composition of the organic product was analyzed by gas chromatography. The results are shown in Table 2.

Embodiment 4

300 ml of a catalyst $La_2O_3$—$Cr_2O_3$ (composing 12 wt % of $La_2O_3$ and 88 wt % of $Cr_2O_3$) is loaded into a first reactor, heated to 270° C., and activated by introducing anhydrous hydrogen fluoride diluted with nitrogen. The flow rate of AHF is 25 g/h, the flow rate of nitrogen is 0.2 L/min, and the activation time is 8 hours.

300 ml of a catalyst $Ga_2O_3$—$Y_2O_3$—$Cr_2O_3$ (composing 7 wt % of $Ga_2O_7$, 9 wt % of $Y_2O_3$ and 84 wt % of $Cr_2O_3$) is loaded into a second reactor, heated to 290° C., and activated by introducing anhydrous hydrogen fluoride diluted with nitrogen. The flow rate of AHF is 25 g/h, the flow rate of nitrogen is 0.2 L/min, and the activation time is 8 hours.

After the activation is completed, HCC-240ab, HCC-240fa and hydrogen fluoride are mixed and then introduced in a vaporizer; the vaporized mixture enters the first reactor for reaction after the temperature of the vaporized mixture is slightly lower than the temperature of the first reactor, wherein the temperature of the first reactor is controlled to be 270° C., the molar ratio of anhydrous hydrogen fluoride to 1,1,1,2,2-pentachloropropane to 1,1,1,3,3-pentachloropropane is 36:2:1, and the contact time is 4s. The material at an outlet of the first reactor is directly sent to the second reactor for reaction, wherein the reaction temperature of the second reactor is 290° C., and the contact time is 4s. A bypass is connected to the outlet of the first reactor for sampling analysis. The product is washed with water and an alkali before analysis. The composition of the organic product is then analyzed by gas chromatography. The results are shown in Table 1. The product at the outlet of the second reactor was washed with water and alkali, and the composition of the organic product was analyzed by gas chromatography. The results are shown in Table 2.

Embodiment 5

300 ml of a catalyst $La_2O_3$—$Cr_2O_3$ (composing 16 wt % of $La_2O_3$ and 84 wt % of $Cr_2O_3$) is loaded into a first reactor, heated to 280° C., and activated by introducing anhydrous hydrogen fluoride diluted with nitrogen. The flow rate of AHF is 25 g/h, the flow rate of nitrogen is 0.2 L/min, and the activation time is 8 hours.

300 ml of a catalyst $Ga_2O_3$—$Y_2O_3$—$Cr_2O_3$ (composing 9 wt % of $Ga_2O_3$, 11 wt % of $Y_2O_3$ and 80 wt % of $Cr_2O_3$) is loaded into a second reactor, heated to 300° C., and activated by introducing anhydrous hydrogen fluoride diluted with nitrogen. The flow rate of AHF is 25 g/h, the flow rate of nitrogen is 0.2 L/min, and the activation time is 8 hours.

After the activation is completed, HCC-240ab, HCC-240fa and hydrogen fluoride are mixed and then introduced in a vaporizer; the vaporized mixture enters the first reactor for reaction after the temperature of the vaporized mixture is slightly lower than the temperature of the first reactor, wherein the temperature of the first reactor is controlled to be 280° C., the molar ratio of anhydrous hydrogen fluoride to 1,1,1,2,2-pentachloropropane to 1,1,1,3,3-pentachloropropane is 20:1:1, and the contact time is 6s. The material at an outlet of the first reactor is directly sent to the second reactor for reaction, wherein the reaction temperature of the second reactor is 300° C., and the contact time is 6s. A bypass is connected to the outlet of the first reactor for sampling analysis. The product is washed with water and an alkali before analysis. The composition of the organic product is then analyzed by gas chromatography. The results are shown in Table 1. The product at the outlet of the second reactor was washed with water and alkali, and the composition of the organic product was analyzed by gas chromatography. The results are shown in Table 2.

Embodiment 6

300 ml of a catalyst $La_2O_3$—$Cr_2O_3$ (composing 18 wt % of $La_2O_3$ and 82 wt % of $Cr_2O_3$) is loaded into a first reactor, heated to 280° C., and activated by introducing anhydrous hydrogen fluoride diluted with nitrogen. The flow rate of AHF is 25 g/h, the flow rate of nitrogen is 0.2 L/min, and the activation time is 8 hours.

300 ml of a catalyst $Ga_2O_3$—$Y_2O_3$—$Cr_2O_3$ (composing 11 wt % of $Ga_2O_3$, 14 wt % of $Y_2O_3$ and 75 wt % of $Cr_2O_3$) is loaded into a second reactor, heated to 320° C., and activated by introducing anhydrous hydrogen fluoride diluted with nitrogen. The flow rate of AHF is 25 g/h, the flow rate of nitrogen is 0.2 L/min, and the activation time is 8 hours.

After the activation is completed, HCC-240ab, HCC-240fa and hydrogen fluoride are mixed and then introduced in a vaporizer; the vaporized mixture enters the first reactor for reaction after the temperature of the vaporized mixture is slightly lower than the temperature of the first reactor, wherein the temperature of the first reactor is controlled to be 280° C., the molar ratio of anhydrous hydrogen fluoride to 1,1,1,2,2-pentachloropropane to 1,1,1,3,3-pentachloropropane is 45:2:1, and the contact time is 2s. The material at an outlet of the first reactor is directly sent to the second reactor for reaction, wherein the reaction temperature of the second reactor is 320° C., and the contact time is 2s. A bypass is connected to the outlet of the first reactor for sampling analysis. The product is washed with water and an alkali before analysis. The composition of the organic product is then analyzed by gas chromatography. The results are shown in Table 1. The product at the outlet of the second reactor was washed with water and alkali, and the composition of the organic product was analyzed by gas chromatography. The results are shown in Table 2.

Embodiment 7

300 ml of a catalyst $La_2O_3$—$Cr_2O_3$ (composing 20 wt % of $La_2O_3$ and 80 wt % of $Cr_2O_3$) is loaded into a first reactor, heated to 300° C., and activated by introducing anhydrous hydrogen fluoride diluted with nitrogen. The flow rate of AHF is 25 g/h, the flow rate of nitrogen is 0.2 L/min, and the activation time is 8 hours.

300 ml of a catalyst $Ga_2O_3$—$Y_2O_3$—$Cr_2O_3$ (composing 13 wt % of $Ga_2O_3$, 17 wt % of $Y_2O_3$ and 70 wt % of $Cr_2O_3$) is loaded into a second reactor, heated to 320° C., and activated by introducing anhydrous hydrogen fluoride diluted with nitrogen. The flow rate of AHF is 25 g/h, the flow rate of nitrogen is 0.2 L/min, and the activation time is 8 hours.

After the activation is completed, HCC-240ab, HCC-240fa and hydrogen fluoride are mixed and then introduced in a vaporizer; the vaporized mixture enters the first reactor for reaction after the temperature of the vaporized mixture is slightly lower than the temperature of the first reactor, wherein the temperature of the first reactor is controlled to be 300° C., the molar ratio of anhydrous hydrogen fluoride to 1,1,1,2,2-pentachloropropane to 1,1,1,3,3-pentachloropropane is 20:1:1, and the contact time is 4s. The material at an outlet of the first reactor is directly sent to the second reactor for reaction, wherein the reaction temperature of the second reactor is 320° C., and the contact time is 4s. A bypass is connected to the outlet of the first reactor for sampling analysis. The product is washed with water and an alkali before analysis. The composition of the organic product is then analyzed by gas chromatography. The results are shown in Table 1. The product at the outlet of the second reactor was washed with water and alkali, and the composition of the organic product was analyzed by gas chromatography. The results are shown in Table 2.

Embodiment 8

300 ml of a catalyst $La_2O_3$—$Cr_2O_3$ (composing 10 wt % of $La_2O_3$ and 90 wt % of $Cr_2O_3$) is loaded into a first reactor, heated to 300° C., and activated by introducing anhydrous hydrogen fluoride diluted with nitrogen. The flow rate of AHF is 25 g/h, the flow rate of nitrogen is 0.2 L/min, and the activation time is 8 hours.

300 ml of a catalyst $Ga_2O_3$—$Y_2O_3$—$Cr_2O_3$ (composing 15 wt % of $Ga_2O_3$, 20 wt % of $Y_2O_3$ and 65 wt % of $Cr_2O_3$)

is loaded into a second reactor, heated to 330° C., and activated by introducing anhydrous hydrogen fluoride diluted with nitrogen. The flow rate of AHF is 25 g/h, the flow rate of nitrogen is 0.2 L/min, and the activation time is 8 hours.

After the activation is completed, HCC-240ab, HCC-240fa and hydrogen fluoride are mixed and then introduced in a vaporizer; the vaporized mixture enters the first reactor for reaction after the temperature of the vaporized mixture is slightly lower than the temperature of the first reactor, wherein the temperature of the first reactor is controlled to be 300° C., the molar ratio of anhydrous hydrogen fluoride to 1,1,1,2,2-pentachloropropane to 1,1,1,3,3-pentachloropropane is 45:1:2, and the contact time is 3.6s. The material at an outlet of the first reactor is directly sent to the second reactor for reaction, wherein the reaction temperature of the second reactor is 330° C., and the contact time is 3.6s. A bypass is connected to the outlet of the first reactor for sampling analysis. The product is washed with water and an alkali before analysis. The composition of the organic product is then analyzed by gas chromatography. The results are shown in Table 1. The product at the outlet of the second reactor was washed with water and alkali, and the composition of the organic product was analyzed by gas chromatography. The results are shown in Table 2.

Embodiment 9

300 ml of a catalyst $La_2O_3$—$Cr_2O_3$ (composing 3 wt % of $La_2O_3$ and 97 wt % of $Cr_2O_3$) is loaded into a first reactor, heated to 300° C., and activated by introducing anhydrous hydrogen fluoride diluted with nitrogen. The flow rate of AHF is 25 g/h, the flow rate of nitrogen is 0.2 L/min, and the activation time is 8 hours.

300 ml of a catalyst $Ga_2O_3$—$Y_2O_3$—$Cr_2O_3$ (composing 15 wt % of $Ga_2O_3$, 20 wt % of $Y_2O_3$ and 65 wt % of $Cr_2O_3$) is loaded into a second reactor, heated to 330° C., and activated by introducing anhydrous hydrogen fluoride diluted with nitrogen. The flow rate of AHF is 25 g/h, the flow rate of nitrogen is 0.2 L/min, and the activation time is 8 hours.

After the activation is completed, HCC-240ab, HCC-240fa and hydrogen fluoride are mixed and then introduced in a vaporizer; the vaporized mixture enters the first reactor for reaction after the temperature of the vaporized mixture is slightly lower than the temperature of the first reactor, wherein the temperature of the first reactor is controlled to be 300° C., the molar ratio of anhydrous hydrogen fluoride to 1,1,1,2,2-pentachloropropane to 1,1,1,3,3-pentachloropropane is 16:1.9:0.1, and the contact time is 3.6s. The material at an outlet of the first reactor is directly sent to the second reactor for reaction, wherein the reaction temperature of the second reactor is 330° C., and the contact time is 4s. A bypass is connected to the outlet of the first reactor for sampling analysis. The product is washed with water and an alkali before analysis. The composition of the organic product is then analyzed by gas chromatography. The results are shown in Table 1. The product at the outlet of the second reactor was washed with water and alkali, and the composition of the organic product was analyzed by gas chromatography. The results are shown in Table 2.

Embodiment 10

300 ml of a catalyst $La_2O_3$—$Cr_2O_3$ (composing 3 wt % of $La_2O_3$ and 97 wt % of $Cr_2O_3$) is loaded into a first reactor, heated to 300° C., and activated by introducing anhydrous hydrogen fluoride diluted with nitrogen. The flow rate of AHF is 25 g/h, the flow rate of nitrogen is 0.2 L/min, and the activation time is 8 hours.

300 ml of a catalyst $Ga_2O_3$—$Y_2O_3$—$Cr_2O_3$ (composing 15 wt % of $Ga_2O_3$, 20 wt % of $Y_2O_3$ and 65 wt % of $Cr_2O_3$) is loaded into a second reactor, heated to 330° C., and activated by introducing anhydrous hydrogen fluoride diluted with nitrogen. The flow rate of AHF is 25 g/h, the flow rate of nitrogen is 0.2 L/min, and the activation time is 8 hours.

After the activation is completed, HCC-240ab, HCC-240fa and hydrogen fluoride are mixed and then introduced in a vaporizer; the vaporized mixture enters the first reactor for reaction after the temperature of the vaporized mixture is slightly lower than the temperature of the first reactor, wherein the temperature of the first reactor is controlled to be 300° C., the molar ratio of anhydrous hydrogen fluoride to 1,1,1,2,2-pentachloropropane to 1,1,1,3,3-pentachloropropane is 16:0.1:1.9, and the contact time is 3.6s. The material at an outlet of the first reactor is directly sent to the second reactor for reaction, wherein the reaction temperature of the second reactor is 330° C., and the contact time is 4s. A bypass is connected to the outlet of the first reactor for sampling analysis. The product is washed with water and an alkali before analysis. The composition of the organic product is then analyzed by gas chromatography. The results are shown in Table 1. The product at the outlet of the second reactor was washed with water and alkali, and the composition of the organic product was analyzed by gas chromatography. The results are shown in Table 2.

TABLE 1

Reaction results of the first reactor

| Embodiments | HCC-240ab | HCC-240fa | HCFO-1233xf | HCFO-1233zd | E-HFO-1234ze | HFO-1234yf | HCC-240 conversion rate (%) |
|---|---|---|---|---|---|---|---|
| 1 | 0 | 0 | 50 | 49.8 | 0.2 | 0 | 100 |
| 2 | 0 | 0 | 49.7 | 49.5 | 0.5 | 0.3 | 100 |
| 3 | 0 | 0 | 49.4 | 47.9 | 2.1 | 0.6 | 100 |
| 4 | 0 | 0 | 65.7 | 31.4 | 2.0 | 0.9 | 100 |
| 5 | 0 | 0 | 48.7 | 46.5 | 3.5 | 1.3 | 100 |
| 6 | 0 | 0 | 65.6 | 30.8 | 2.6 | 1.0 | 100 |
| 7 | 0 | 0 | 46.6 | 44.9 | 5.1 | 3.4 | 100 |
| 8 | 0 | 0 | 29.6 | 60.0 | 6.6 | 3.8 | 100 |
| 9 | 0 | 0 | 94.9 | 4.8 | 0.2 | 0.1 | 100 |
| 10 | 0 | 0 | 4.9 | 93.9 | 1.1 | 0 | 100 |

TABLE 2

Reaction results of the second reactor

| | Reaction conditions | | Organic composition of the reaction product | | | | HFO-1234yf + E-HFO-1234ze |
|---|---|---|---|---|---|---|---|
| Embodiments | Reaction temperature (° C.) | Contact time (s) | HCFO-1233xf | HCFO-1233zd | E-HFO-1234ze | HFO-1234yf | selectivity (%) |
| 1 | 280 | 10 | 1.3 | 0.4 | 49.6 | 48.7 | 98.3 |
| 2 | 280 | 7.2 | 1.5 | 0.5 | 49.5 | 48.5 | 98.0 |
| 3 | 290 | 6 | 1.2 | 0.3 | 49.7 | 48.8 | 98.5 |
| 4 | 290 | 4 | 1.3 | 0.2 | 33.1 | 65.4 | 98.5 |
| 5 | 300 | 6 | 0.9 | 0 | 50.0 | 49.1 | 99.1 |
| 6 | 320 | 2 | 0.7 | 0 | 33.3 | 66.0 | 99.3 |
| 7 | 320 | 4 | 0.8 | 0 | 50.0 | 49.2 | 99.2 |
| 8 | 330 | 3.6 | 0.6 | 0 | 66.6 | 32.8 | 99.4 |
| 9 | 330 | 4 | 0.3 | 0 | 4.9 | 94.4 | 99.3 |
| 10 | 330 | 4 | 0.2 | 0 | 95.0 | 4.7 | 99.7 |

What is claimed is:

1. A method for co-producing 2,3,3,3-tetrafluoropropene and trans-1,3,3,3-tetrafluoropropene, comprising following steps of:

(1) preheating a mixture of 1,1,1,2,2-pentachloropropane and 1,1,1,3,3-pentachloropropane together with anhydrous hydrogen fluoride and simultaneously introducing into a first reactor to react in the presence of a catalyst $La_2O_3$—$Cr_2O_3$ at a reaction temperature of 200-350° C., with a contact time of 1-20s to obtain a first reactor product, wherein a molar ratio of the anhydrous hydrogen fluoride to the mixture of 1,1,1,2,2-pentachloropropane and 1,1,1,3,3-pentachloropropane is 6-18:1;

(2) directly introducing the first reactor product obtained in the step (1) into a second reactor without separation, and carrying out a catalytic fluorination reaction in the presence of a catalyst $Ga_2O_3$—$Y_2O_3$—$Cr_2O_3$ at a reaction temperature of 250-400° C., with a contact time of 1-35s to obtain a second reactor product;

(3) introducing the second reactor product obtained in the step (2) into a first separation column for separation to obtain a bottom component of a first separation column and hydrogen chloride;

(4) introducing the bottom component of the first separation column obtained in the step (3) into a second separation column for separation to obtain an overhead component of the second separation column and a bottom component of the second separation column;

(5) washing the overhead component of the second separation column obtained in the step (4) with water and an alkali, drying, and then introducing into a third separation column to obtain an overhead component of the third separation column and a bottom component of the third separation column;

(6) introducing the bottom component of the third separation column obtained in the step (5) into a fourth separation column to obtain a 2,3,3,3-tetrafluoropropene product and a bottom component of the fourth separation column; and (7) introducing the bottom component of the fourth separation column obtained in the step (6) into a fifth separation column to obtain a trans-1,3,3,3-tetrafluoropropene product.

2. The method for co-producing 2,3,3,3-tetrafluoropropene and trans-1,3,3,3-tetrafluoropropene according to claim 1, wherein in the step (1), a molar ratio of 1,1,1,2,2-pentachloropropane to 1,1,1,3,3-pentachloropropane in the mixture of 1,1,1,2,2-pentachloropropane and 1,1,1,3,3-pentachloropropane is 1:0.05-20.

3. The method for co-producing 2,3,3,3-tetrafluoropropene and trans-1,3,3,3-tetrafluoropropene according to claim 1, wherein in the step (1), the molar ratio of the anhydrous hydrogen fluoride to the mixture of 1,1,1,2,2-pentachloropropane and 1,1,1,3,3-pentachloropropane is 8-15:1, the reaction temperature is 250-300° C., and the contact time is 2-10s.

4. The method for co-producing 2,3,3,3-tetrafluoropropene and trans-1,3,3,3-tetrafluoropropene according to claim 1, wherein in the step (2), the reaction temperature is 280-330° C., and the contact time is 4-15s.

5. The method for co-producing 2,3,3,3-tetrafluoropropene and trans-1,3,3,3-tetrafluoropropene according to claim 1, wherein in the step (1), the catalyst $La_2O_3$—$Cr_2O_3$ comprises 0.5-20 wt % of $La_2O_3$ and 80-99.5 wt % of $Cr_2O_3$.

6. The method for co-producing 2,3,3,3-tetrafluoropropene and trans-1,3,3,3-tetrafluoropropene according to claim 1, wherein in the step (2), the catalyst $Ga_2O_3$—$Y_2O_3$—$Cr_2O_3$ comprises 1-15 wt % of $Ga_2O_3$, 3-20 wt % of $Y_2O_3$ and 65-96 wt % of $Cr_2O_3$.

7. The method for co-producing 2,3,3,3-tetrafluoropropene and trans-1,3,3,3-tetrafluoropropene according to claim 1, wherein in the step (4), the bottom component of the second separation column is circulated to the first reactor.

* * * * *